United States Patent [19]

Lütjens et al.

[11] Patent Number: 4,997,974
[45] Date of Patent: Mar. 5, 1991

[54] BISPHENOL DERIVATIVES AND POLYMERS THEREOF

[75] Inventors: Holger Lütjens, Cologne; Uwe Westeppe, Mettmann; Karl-Erwin Piejko, Bergisch Gladbach; Christian Lindner, Cologne, all of Fed. Rep. of Germany

[73] Assignee: Bayer Aktiengesellschaft, Leverkusen, Fed. Rep. of Germany

[21] Appl. No.: 569,652

[22] Filed: Aug. 20, 1990

[30] Foreign Application Priority Data

Aug. 30, 1989 [DE] Fed. Rep. of Germany ....... 3928658

[51] Int. Cl.$^5$ .............................................. C07G 69/76
[52] U.S. Cl. ...................................... 560/57; 526/311; 526/313; 528/193
[58] Field of Search ................ 526/313, 311; 528/193; 560/57

[56] References Cited
FOREIGN PATENT DOCUMENTS
0105467 9/1978 Japan .

Primary Examiner—Joseph L. Schofer
Assistant Examiner—Fred Zitomer
Attorney, Agent, or Firm—Connolly and Hutz

[57] ABSTRACT

Bisphenol derivatives corresponding to formula (I)

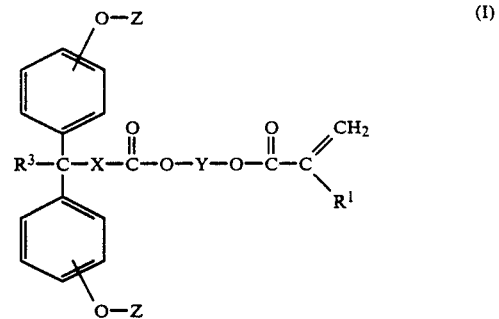

in which
$R^1$ is hydrogen, $C_{1-4}$ alkyl,
$R^2$ is $C_{1-12}$ alkyl,
$R^3$ is $C_{1-12}$ alkyl,
X is $C_{1-12}$ alkylene,
Y is $C_{1-12}$ alkylene,
Z is hydrogen,

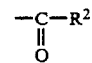

and polymers produced thereform containing structural units corresponding to formula (II)

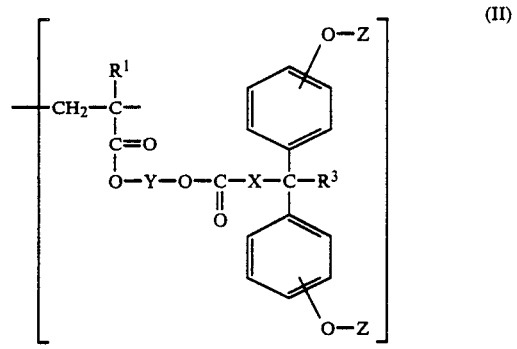

in which $R^1$, $R^2$, $R^3$, X, Y and Z are as defined above.

2 Claims, No Drawings

BISPHENOL DERIVATIVES AND POLYMERS THEREOF

This invention relates to special bisphenol derivatives and to polymers produced therefrom. The polymers containing these bisphenols in polymerized form show special properties and have potential industrial applications.

More particularly, the present invention relates to bisphenol derivatives corresponding to formula (I)

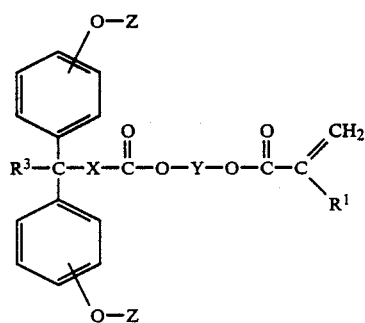

in which
R$^1$ is hydrogen, C$_{1-4}$ alkyl (preferably methyl),
R$^2$ is C$_{1-12}$ alkyl (preferably methyl),
R$^3$ is C$_{1-12}$ alkyl,
X is C$_{1-12}$ alkylene, preferably C$_{1-8}$ alkylene,
Y is C$_{1-12}$ alkylene, preferably C$_{1-8}$ alkylene,
Z is H,

The invention also relates to polymers containing structural units corresponding to formula (II)

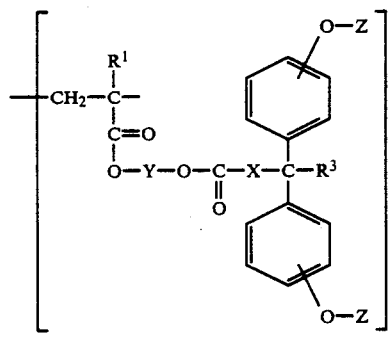

in which R$^1$, R$^2$, R$^3$, X, Y and Z are as defined above.

The bisphenol derivatives of formula (I) according to the invention may be prepared by reaction of a bis-(4-acetoxyphenyl)-carboxylic acid or a derivative corresponding to formula (III) with a hydroxyalkyl acrylate corresponding to formula (IV):

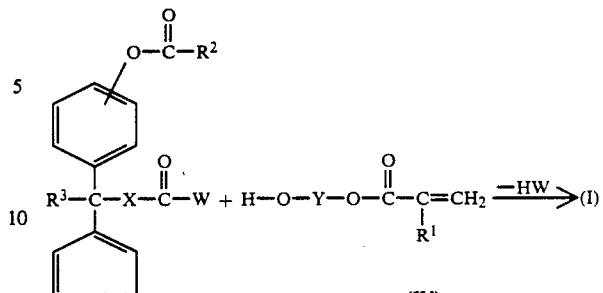

in which
R$^1$, R$^2$, R$^3$, X, and Y are as defined above and
W represents OH, OR$^4$, N(R$^4$)$_2$, Hal (preferably Cl) and
R$^4$ represents C$_{1-12}$ alkyl.

Preferred derivatives corresponding to formula (III) are the carboxylic acid chlorides (W=Cl).

Hydroxyalkyl acrylates of formula (IV) suitable as starting products are, for example,

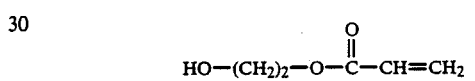

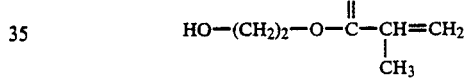

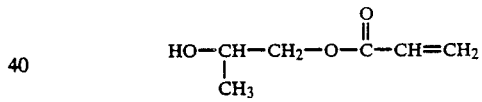

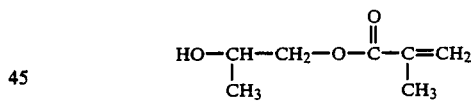

while suitable carboxylic acid halides of formula (III) are, for example,

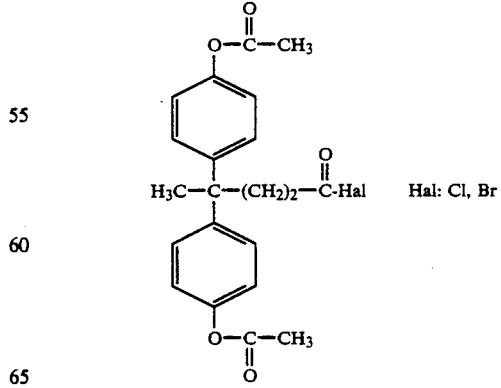

The polymers according to the invention containing structural units of formula (II) are homopolymers of the bisphenol derivatives corresponding to formula (I) or copolymers containing structural units of formula (II) in addition to other structural units. The copolymers according to the invention contain structural units of formula (II) in quantitites of from 1 to 99% by weight. The other structural units present in the copolymers are preferably derived from the following monomers:

(a) vinyl compounds, such as styrene, α-methyl styrene, halostyrenes, methoxystyrenes,
(b) vinyl halides, such as vinyl chloride, vinyl fluoride, vinylidene chloride,
(c) vinyl alkyl ketones, such as vinyl methyl ketone,
(d) vinyl esters of organic acids, such as for example vinyl acetate, vinyl butyrate, vinyl propionate,
(e) α,β-unsaturated carboxylic acids, such as acrylic acid, methacrylic acid, itaconic acid, maleic acid,
(f) derivatives of acrylic acid and methacrylic acid, such as acrylonitrile, methacrylonitrile, acrylic acid amide, methacrylic acid amide, N-methylol acrylamide, N-methylol methacrylamide, dimethylaminopropylamide,
(g) $C_{1-14}$ alkyl acrylates, such as methyl, ethyl, butyl, octyl, 2-ethyl hexyl acrylate, chloroethyl acrylate, benzyl acrylate, phenyl ethyl acrylate; $C_{1-8}$ alkyl methacrylates which may optionally be substituted in the alkyl radical by such functional groups as hydroxyl, epoxide, oxetane, amine groups, for example methyl methacrylate, cyclohexyl methacrylate, glycidyl methacrylate, hydroxyethyl methacrylate, hydroxypropyl methacrylate, dimethylaminoethyl methacrylate; maleic anhydride,
(h) polymerized olefins and dienes, such as isobutylene, butadiene, isoprene, propylene, chloroprene,
(i) vinyl alkyl ethers.

The polymers according to the invention may be prepared in known manner by polymerization of the bisphenol derivatives of formula (I) according to the invention and, optionally, the comonomers mentioned above. The polymerization is preferably carried out as solution, suspension or emulsion polymerization, preferably in the presence of radical initiators. Suitable radical initiators are, for example, compounds containing azo groups, such as azoisobutyrodinitrile, 4,4-azobis-(4-cyanovaleric acid), organic peroxides, such as benzoyl peroxide, tert.-butyl hydroperoxide, dibenzoyl peroxide, and inorganic peroxide salts, such as potassium peroxodisulfate, ammonium peroxodisulfate.

If the polymerization is carried out in solution, solvents in which only the monomers are soluble or in which both the monomers and the polymers are soluble may be used. Suitable organic solvents are, for example, butanol, methyl ethyl ketone, ethylbenzene.

If the polymerization is carried out in (aqueous) emulsion, the monomers are best emulsified with emulsifiers, for example anionic, cationic or nonionic emulsifiers, for example sodium, potassium, ammonium salts of fatty acids, sodium lauryl sulfate, the sodium salt of $C_{14}$–$C_{18}$ alkyl sulfonic acids, oleyl or octadecyl alcohol.

Polymerization is advantageously carried out at elevated temperature, for example at +30° to +90° C. and more especially at +60° to +85° C.

For polymerization, the substituents Z in the bisphenol derivatives corresponding to formula (I) are preferably

which also remain intact during the polymerization; free phenol groups can inhibit the polymerization. Strongly acidic medium (pH <1) and strongly alkaline medium (pH >12) and relatively high temperatures should also be avoided where polymerization is carried out in emulsion. The polymerization is preferably carried out in mildly acidic or neutral medium.

The molecular weight of the polymers according to the invention may be regulated in a known manner through the polymerization temperature, through the monomer concentration, through the quantity of catalyst and by molecular weight regulators. Preferred molecular weight regulators are organosulfur compounds, for example mercaptans or disulfides, more especially long-chain mercaptans, such as nand tert.-dodecyl mercaptans. They are normally dissolved in the monomer. The molecular weights $\overline{M}w$ (weight average) of the polymers according to the invention (as determined by light scattering or sedimentation) are in the range from 1,000 to 5,000,000 g/mol.

The substituents

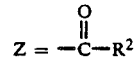

in the polymers according to the invention may be hydrolyzed by bases, so that structural units corresponding to formula (II) with Z=H are formed.

For hydrolysis, a base may initially be added to the polymerization mixture (for example the emulsion) on completion of polymerization without isolation of the polymers and the emulsion subsequently heated for a prolonged period, for example for 3 hours to 3 days and preferably for 12 to 24 hours, at temperatures in the range from 30° to 95° C. and preferably at temperatures in the range from 50° to 90° C., followed by isolation of the polymers by coagulation or precipitation. Suitable bases are alkali metal hydroxides, for example potassium hydroxide, sodium hydroxide, ammonium hydroxide, quaternary ammonium bases, for example tetramethyl ammonium hydroxide, benzyl trimethyl ammonium hydroxide, and water-soluble amines, for example methylamine, ethylamine, dimethylamine, diethylamine, benzyl methylamine.

The polymers according to the invention may be used as epoxy resins after reaction of the phenolic groups with epichlorohydrin. They are also suitable as epoxy resin crosslinkers and, in addition, may be used in the production of photoresists. They also act as migration-resistant polymeric stabilizers (antioxidants) by virtue of their phenolic groups.

EXAMPLES

EXAMPLE 1.1

224 g (2.2 mol) ACETIC ANHYDRIDE are added with stirring at room temperature to 286 g (1 mol) 4,4-bis-(4-hydroxyphenyl)-valeric acid (95%, Aldrich-Chemie). After stirring for 2 hours at 100° C., the reaction mixture is poured onto ice and extracted with methylene chloride. The organic extracts are washed with aqueous sodium hydrogen carbonate solution and water and dried and the solvent is distilled off. The solid crude product remaining is washed with cold toluene and hexane.

Yield: 295 g (80%).

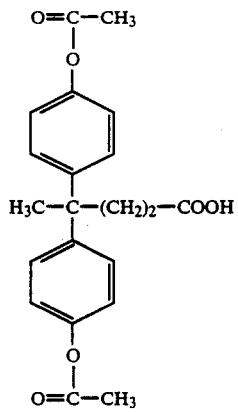

Melting point: 140°–142° C.

EXAMPLE 1.2

45 g (0.38 mol) thionyl chloride and 1 drop dimethyl formamide are added to 93 g (0.25 mol) as in Example 1.1. The reaction mixture is slowly heated with stirring to 90° C. and kept at that temperature for 1 hour. The excess thionyl chloride is then distilled off in vacuo and the solid residue remaining is washed with cold toluene and hexane.

Yield 84 g (85%)

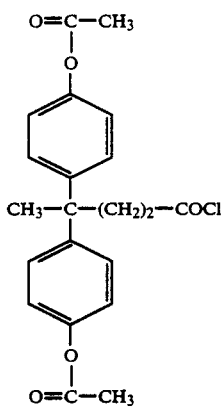

Melting point: 113° C.

EXAMPLE 1.3 (invention)

A solution of 195 g (0.5 mol) according to Example 1.2 in 400 ml methylene chloride is slowly added dropwise with stirring at 0° C. to a solution of 65 g (0.2 mol) 2-hydroxyethyl methacrylate and 62 g (0.6 mol) triethylamine in 300 ml methylene chloride, followed by stirring for 12 hours at room temperature. After the insoluble material has been filtered off, the methylene chloride is distilled off, leaving a clear, viscous, pale yellowish oil.

Yield: 225 g (90%)

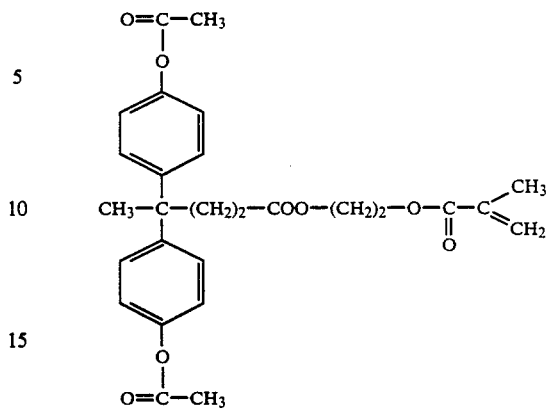

The product is analyzed as follows:

IR (film): $\nu = 3000$, 1760, 1740, 1640, 1610, 1510, 1370, 1320, 1300, 1200, 1170, 1020, 920, 850 cm$^{-1}$. $^1$H-NMR (CDCl$_3$, TMS): $\delta = 7.20$ (m; 4H), 7.00 (m: 4H), 6.13 (m: 1H), 5.60 (m; 1H), 4.30 (m; 4H), 2.42 (m; 2H), 2.30 (s; 6H), 2.15 (m; 2H), 1.95 (s; 3H), 1.60 (s; 3H) ppm. m=multiplet, s=singlet. TMS: tetramethyl silane. MW theoretical: 482 g/mol. MW vapor pressure osmometry: 479 g/mol.

EXAMPLE 1.4

The procedure is as in Example 1.3 using 2-hydroxyethyl acrylate instead of the 2-hydroxyethyl methacrylate.

Yield: 217 g (87%)

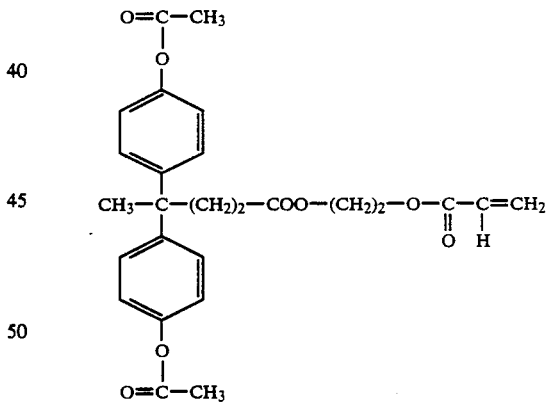

Viscous oil. IR (film): $\nu = 3000$, 1760, 1730, 1640, 1610, 1500, 1410, 1370, 1200, 1040, 1020, 910, 850 cm$^{-1}$. MW theoretical: 468 g/mol. MW vapor pressure osmometry: 462 g/mol.

EXAMPLE 2 (invention)

0.26 Part by weight azoisobutyronitrile is added to a solution of 13 parts by weight of the following monomer mixtures in 52 parts by weight ethylbenzene, followed by heating with stirring under nitrogen for 15 hours at 65° C. The solution is then stirred into methanol and the polymer precipitated is filtered off and dried.

| Example | Monomer mixture: Monomer of Example 1.3 parts by weight | Styrene parts by weight | MMA parts by weight | n-BA parts by weight |
|---|---|---|---|---|
| 2.1 | 13 | — | — | — |
| 2.2 | 10 | 3 | — | — |
| 2.3 | 10 | — | 3 | — |
| 2.4 | 10 | — | — | 3 |

MMA: methyl methacrylate; n-BA: n-butyl acrylate

Yield: Example 2.1: 10.8 parts by weight (83%). Example 2.2: 12.0 parts by weight (92%). Example 2.3: 12.3 parts by weight (95%). Example 2.4: 12.4 parts by weight (93%).

The polymer of Example 2.1 has the following analysis:

| Calculated | Found |
|---|---|
| C = 67.2% | C = 67.8% |
| H = 6.3% | H = 6.4% |

The polymer contains the following structural units:

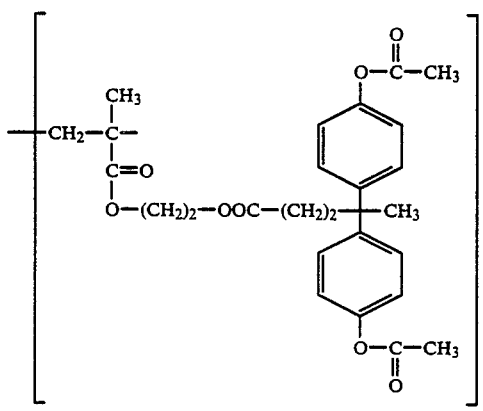

Its composition is as follows:

| Polymer | % by weight monomer 1.3 in the polymer |
|---|---|
| 2.1 | 100 |
| 2.2 | 71 |
| 2.3 | 73 |
| 2.4 | 72 | as determined by gas-chromatographic residual monomer determination and gel permeation chromatography (GPC).

The polymers of Example 2.1 to 2.4 have the following properties:

| Polymer | $[\eta]_{DMF}$ | Appearance at room temperature |
|---|---|---|
| 2.1 | 0.63 | Colorless powder |
| 2.2 | 0.71 | Colorless powder |
| 2.3 | 0.73 | Colorless powder |
| 2.4 | 0.78 | Colorless powder |

The polymers are soluble, for example in dimethyl formamide, tetrahydrofuran, acetone; the solutions formed can be cast to form transparent films.

The chemical uniformity of the copolymers according to Example 2.2 to 2.4 was verified by gel permeation chromatography (GPC).

$[\eta]$ Intrinsic viscosity measured in dimethyl formamide at 25° C.

EXAMPLE 3 (invention)

20 Parts by weight of the product of Example 1.3 are emulsified in a solution of 0.4 part by weight of the sodium salt of $C_{14-18}$ alkyl sulfonic acids in 45 parts by weight water and, after the addition of 0.1 part by weight tert.-dodecyl mercaptan, the emulsion is heated to 75° C. After the addition of 0.09 part by weight potassium peroxodisulfate, the emulsion is stirred for 10 hours at 75° C. A latex having a solids content of 30% is obtained. The emulsion is coagulated with an aqueous magnesium sulfate solution and the polymer filtered off is washed and dried. Yield: 17 parts by weight (85%).

The product has an intrinsic viscosity $[\eta]$ of 0.8 (as measured in dimethyl formamide). The polymer is identical in structure with that of Example 2.1.

The polymer is soluble in tetrahydrofuran, dimethyl formamide and acetone, but insoluble in toluene, methylene chloride and water.

The polymer may be used for the production of transparent cast films.

EXAMPLE 4 (invention)

6 Parts by weight concentrated aqueous ammonia solution (25%) are added to 50 parts by weight of the emulsion of Example 3 (solids content: 30%) and, after dilution with 70 parts by weight water, the reaction mixture is stirred for 18 hours at 70° C. The reaction mixture is then adjusted with dilute aqueous hydrochloric acid to pH 3 and the solid precipitated is filtered off, washed with water and dried.

Yield: 11 parts by weight (90%). IR (KBr): $\upsilon=3650-3100$, 3000, 1740, 1620, 1600, 1510, 1440, 1240, 1180, 840 cm$^{-1}$.

The polymer forms highly viscous, free-flowing solutions in aqueous sodium hydroxide; for example, solid films may be cast from 10% by weight solutions.

In other words, the sodium salt of the new polymer is readily soluble in water while the free phenol is sparingly soluble at room temperature.

The polymer is almost completely hydrolyzed and thus consists predominantly of the following structural unit:

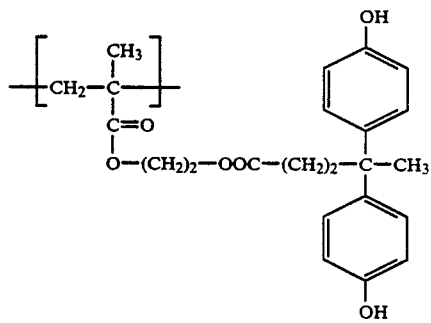

EXAMPLE 5

5 Parts by weight of the polymer of Example 3 are heated for 4 hours to 125° C. with 2.5 parts by weight bisphenol A diglycidyl ether and 0.015 part by weight sodium hydroxide. The melt hardens and forms the epoxy resin. More than 60% of the polymer of Example 3 used may be separated from the epoxy resin.

EXAMPLE 6

5 Parts by weight of the polymer of Example 4 are heated for 4 hours to 125° C. with 2.5 parts by weight bisphenol A diglycidyl ether and 0.015 part by weight sodium hydroxide. This results in formation of the epoxy resin from which the polymer of Example 4 cannot be removed by solvent extraction. Accordingly, the polymer of Example 4 has reacted with the epoxide with crosslinking.

We claim:

1. Bisphenol derivatives corresponding to formula (I)

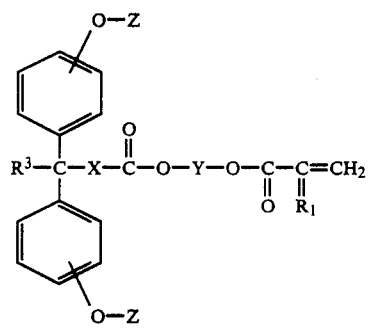

in which
$R^1$ is hydrogen, $C_{1-4}$ alkyl,
$R^2$ is $C_{1-12}$ alkyl,
$R^3$ is $C_{1-12}$ alkyl,
X is $C_{1-12}$ alkylene,
Y is $C_{1-12}$ alkylene,
Z is hydrogen,

2. Polymers containing structural units corresponding to formula (II)

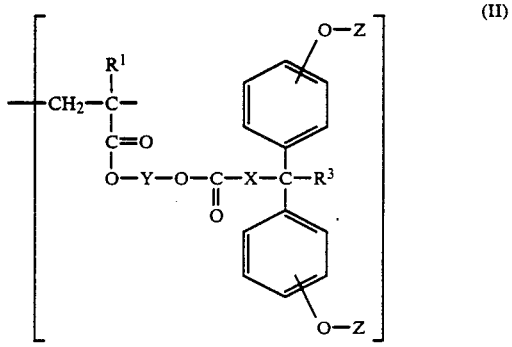

in which $R^1$, $R^2$, $R^3$, X, Y and Z are as defined in claim 1.

* * * * *